United States Patent
Van Snellenberg et al.

(10) Patent No.: US 12,268,473 B2
(45) Date of Patent: Apr. 8, 2025

(54) DEVICE FOR NON-INVASIVE DETECTION OF SKIN PROBLEMS ASSOCIATED WITH DIABETES MELLITUS

(71) Applicant: Signify Health, LLC, Dallas, TX (US)

(72) Inventors: Mike Van Snellenberg, Seattle, WA (US); Anne Weiler, Seattle, WA (US); Luke Feaster, Seattle, WA (US); Ben Spencer, Seattle, WA (US); Jahyen Chung, Bellevue, WA (US); Sara Hansen-Lund, Seattle, WA (US); Soma Mandal, Seattle, WA (US); Josh Bishop, Seattle, WA (US); Gavin Ray, Seattle, WA (US)

(73) Assignee: Signify Health, LLC, Dallas, TX (US)

( * ) Notice: Subject to any disclaimer, the term of this patent is extended or adjusted under 35 U.S.C. 154(b) by 100 days.

(21) Appl. No.: 17/752,755

(22) Filed: May 24, 2022

(65) Prior Publication Data

US 2022/0280100 A1  Sep. 8, 2022

Related U.S. Application Data

(62) Division of application No. 16/044,248, filed on Jul. 24, 2018, now abandoned.

(Continued)

(51) Int. Cl.
*A61B 5/00* (2006.01)
*A61B 5/01* (2006.01)
(Continued)

(52) U.S. Cl.
CPC .......... *A61B 5/0077* (2013.01); *A61B 5/0035* (2013.01); *A61B 5/0053* (2013.01);
(Continued)

(58) Field of Classification Search
CPC ................ A61B 5/0077; A61B 5/4827; A61B 5/44–449
See application file for complete search history.

(56) References Cited

U.S. PATENT DOCUMENTS

| | | | |
|---|---|---|---|
| 5,938,593 | A | 8/1999 | Ouellette |
| 6,767,330 | B2 | 7/2004 | Lavery et al. |

(Continued)

FOREIGN PATENT DOCUMENTS

WO   WO-2006026548 A1 * 3/2006 ............... A61B 5/16

OTHER PUBLICATIONS

Goyal et al., Fully Convolutional Networks for Diabetic Foot Ulcer Segmentation arXiv:1708.01928v1 Aug. 6, 2017 (Year: 2017).*

(Continued)

*Primary Examiner* — Colin T. Sakamoto
(74) *Attorney, Agent, or Firm* — CHRISTENSEN O'CONNOR JOHNSON KINDNESS PLLC (57) ABSTRACT

A medical diagnostic apparatus includes a controller; a user interface; a platform having a horizontal surface; and at least one visible light image sensor positioned below the horizontal surface that is capable of producing a diagnostic visible light image of a bottom portion of a foot or feet positioned on the horizontal surface. At least a portion of the horizontal surface is transparent to visible light. The apparatus may further include at least one infrared image sensor positioned below the horizontal surface that is capable of producing a thermal image of the first target area. The apparatus may further include sensors positioned above the platform capable of producing diagnostic visible light images or thermal images of a top portion of the user's foot or feet. The apparatus may further include a weight measurement system coupled to the platform.

18 Claims, 6 Drawing Sheets

Related U.S. Application Data (60) Provisional application No. 62/536,388, filed on Jul. 24, 2017.

(51) Int. Cl.

| | |
|---|---|
| *G01G 19/50* | (2006.01) |
| *G06T 7/00* | (2017.01) |
| *G16H 30/20* | (2018.01) |
| *G16H 30/40* | (2018.01) |
| *G16H 40/63* | (2018.01) |
| *G16H 50/20* | (2018.01) |
| *H04N 5/33* | (2023.01) |
| *G06F 18/24* | (2023.01) |
| *G06T 7/70* | (2017.01) |

(52) U.S. Cl.
CPC ............ *A61B 5/015* (2013.01); *A61B 5/4041* (2013.01); *A61B 5/441* (2013.01); *A61B 5/445* (2013.01); *A61B 5/4827* (2013.01); *A61B 5/6829* (2013.01); *A61B 5/6887* (2013.01); *A61B 5/7267* (2013.01); *A61B 5/741* (2013.01); *G01G 19/50* (2013.01); *G06T 7/0012* (2013.01); *G16H 30/20* (2018.01); *G16H 30/40* (2018.01); *G16H 40/63* (2018.01); *G16H 50/20* (2018.01); *H04N 5/33* (2013.01); *A61B 5/706* (2013.01); *A61B 5/7405* (2013.01); *A61B 5/742* (2013.01); *A61B 2562/0252* (2013.01); *G06F 18/24* (2023.01); *G06T 7/70* (2017.01); *G06T 2207/20081* (2013.01); *G06T 2207/20084* (2013.01); *G06T 2207/30088* (2013.01); *G06T 2207/30168* (2013.01); *G06V 2201/03* (2022.01)

(56) References Cited

U.S. PATENT DOCUMENTS

| | | |
|---|---|---|
| 2002/0082486 A1 | 6/2002 | Lavery et al. |
| 2007/0016079 A1 | 1/2007 | Freeman et al. |
| 2007/0038042 A1 | 2/2007 | Freeman et al. |
| 2008/0083416 A1 | 4/2008 | Xia et al. |
| 2008/0183096 A1* | 7/2008 | Snyder .................. G16H 50/70 600/545 |
| 2008/0193905 A1* | 8/2008 | Leung ................... G09B 23/30 901/46 |
| 2010/0177968 A1* | 7/2010 | Fry ................. G08B 13/19697 600/509 |
| 2013/0162796 A1 | 6/2013 | Bharara et al. |
| 2013/0289889 A1 | 10/2013 | Yuen et al. |
| 2014/0121479 A1 | 5/2014 | O'Connor et al. |
| 2015/0374306 A1* | 12/2015 | Gelbman ............. G06V 40/171 600/476 |
| 2019/0200917 A1* | 7/2019 | Murphy ................ A61B 5/441 |

OTHER PUBLICATIONS

Goyal et al., DFUNet: Convolutional Neural Networks for Diabetic Foot Ulcer Classification arXiv:1711.10448v2 Dec. 10, 2017 (Year: 2017).*

Bagavathiappan, S., et al., "Infrared Thermal Imaging for Detection of Peripheral Vascular Disorders," Journal of Medical Physics 34(1):43-47, Jan.-Mar. 2009.

Bienvenu, C., "Smart Foot Mat Allows Earlier Detection of Diabetic Foot Ulcers in Real-World Study," Jul. 6, 2017, <https://www.diabetes.co.uk/news/2017/jul/smart-foot-mat-allows-earlier-detection-of-diabetic-foot-ulcers-in-real-world-study-94809707.html> [retrieved Nov. 8, 2018], 5 pages.

Siddiqui, H.-U.-R., et al., "Automated Peripheral Neuropathy Assessment of Diabetic Patients Using Optical Imaging and Binary Processing Techniques," Proceedings of the 2013 IEEE Point-of-Care Healthcare Technologies (PHT), Jan. 16-18, 2013, Bangalore, India, 4 pages.

* cited by examiner

DEVICE FOR NON-INVASIVE DETECTION OF SKIN PROBLEMS ASSOCIATED WITH DIABETES MELLITUS

CROSS-REFERENCE TO RELATED APPLICATION

This application is a division of U.S. patent application Ser. No. 16/044,248, filed Jul. 24, 2018, which claims the benefit of U.S. Provisional Application No. 62/536,388, filed Jul. 24, 2017, the entire disclosure of which is hereby incorporated by reference herein for all purposes.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a medical diagnostic apparatus includes a controller; a user interface configured for user interaction with the medical diagnostic apparatus; a platform having a horizontal surface; a weight measurement system coupled to the platform; and at least one visible light image sensor positioned below the horizontal surface that is capable of producing a diagnostic visible light image of a bottom portion of a foot or feet positioned on the horizontal surface. At least a portion of the horizontal surface is transparent to visible light.

In an embodiment, at least a portion of the horizontal surface is transparent to infrared light suitable for thermal imaging, and the apparatus further includes at least one infrared image sensor positioned below the horizontal surface that is capable of producing a thermal image of the first target area.

In an embodiment, the apparatus further includes at least one visible light image sensor positioned above the platform capable of producing a diagnostic visible light image of a top portion of the user's foot or feet.

In an embodiment, the apparatus further includes at least one infrared image sensor positioned above the platform capable of producing a thermal image of a top portion of the user's foot or feet.

In another aspect, a medical diagnostic apparatus includes a platform having a horizontal surface; at least one upper image sensor positioned above the horizontal surface and configured to capture one or more images of a top portion of a foot or feet; at least one lower image sensor positioned below the horizontal surface and configured to capture one or more images of a bottom portion of the foot or feet; a controller; and a user interface configured for user interaction with the medical diagnostic apparatus. At least a portion of the horizontal surface is transparent to visible light. In an embodiment, two cameras area are positioned below the horizontal surface. In an embodiment, at least a portion of the horizontal surface is transparent to infrared light suitable for thermal imaging, and the medical diagnostic apparatus further includes at least one infrared image sensor positioned below the horizontal surface that is capable of producing a thermal image of the bottom portion of the foot or feet.

In any of the described embodiments, a medical diagnostic apparatus may include a device for testing for peripheral neuropathy. The device may include a controller; a foot platform having at least one opening; at least one vertically oriented monofilament positioned to pass through the at least one opening of the foot platform; and at least one actuator positioned below the at least one opening of the foot platform. The at least one actuator is mechanically coupled to the at least one vertically oriented monofilament and is configured to move the at least one vertically oriented monofilament to pass through the at least one opening of the foot platform.

In any of the described embodiments, a medical diagnostic apparatus may include a visual or tactile guide for foot positioning, one or more illumination sources, or a combination of these or other additional features.

In another aspect, a computer-implemented method is described for automated diagnosis of a diabetic foot condition. The method includes capturing, by one or image capture devices of a medical diagnostic apparatus, optical image data of a target area of a foot; collecting, by a touch sensitivity testing device (e.g., a servo-actuated monofilament probe) of the medical diagnostic apparatus, physical touch sensitivity data for the target area of the foot; transmitting, by the medical diagnostic apparatus, the optical image data, the physical touch sensitivity data, or a combination of such data to an analysis engine; and outputting, by the analysis engine, one or more indications of a diabetic foot condition. The method may further include checking the optical image data one or more of image quality, lighting conditions, or body positioning. The method may further include, prior to collecting the physical touch sensitivity data, confirming the position of the foot based at least in part on the optical image data. The analysis engine may include an image classifier.

In any of the described embodiments, a user interface may include an interactive voice interface, a display, a visual indicator, a combination of such user interface features, or other user interface features.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present disclosure describes embodiments that facilitate non-invasive detection of skin problems in the feet or other areas, including neuropathy, vascular disease, and ulcers, such as those associated with diabetes mellitus.

In the following description, numerous specific details are set forth in order to provide a thorough understanding of illustrative embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein. The illustrative examples provided herein are not intended to be exhaustive or to limit the claimed subject matter to the precise forms disclosed.

Diabetic foot infection is the most common complication of diabetes mellitus leading to hospitalization and the most frequent cause of non-traumatic lower extremity amputation. Diabetic foot ulcers and other foot infections develop due to reduced feeling in the foot from peripheral neuropathy, the most common form of diabetic neuropathy. People that suffer from such conditions may not be aware of abrasions or hotspots that may develop into ulcers, that wounds are not healing, or that foreign objects have become lodged in the foot.

To address problems such as these, disclosed embodiments use a combination of sensors (e.g., optical and physical sensors) combined with related processing techniques (e.g., machine-learned classifiers) to help detect skin conditions (e.g., possible complications from diabetes). As described in detail below, the user or patient may be guided through operation of the device using an interactive voice system.

One possible sensing mechanism that may be used in disclosed embodiments is a group of low-cost image sensors (e.g., in commercially available cameras), capturing visible spectrum or near-IR images. In a disclosed embodiment, cameras are arranged in pairs (e.g., with one above and one below the subject body part being measured). Many-camera setups can also be used to enhance the camera coverage and increase the accuracy of the prediction algorithms. Single-camera applications are also possible, though in practice the user may need to reposition his body to get full camera coverage of the body part in question. The disclosed image sensors and cameras may be used alone, or in combination with other sensing systems.

A second sensing mechanism that may be used in disclosed embodiments uses a thermographic infrared image sensor (e.g., in commercially available infrared cameras) for detecting areas of varying skin temperature which can help identify regions that are either cooler-than-surrounding areas (which may indicate conditions such as compromised blood flow) or hotter-than-surrounding areas (which may indicate conditions such as active infections). In a disclosed embodiment, the infrared image sensors (e.g., in one or more thermal cameras) are co-located with the visible-spectrum image sensors (e.g., with one infrared camera above and one below the subject body part being measured).

A third sensing mechanism that may be used in disclosed embodiments is a physical sensor. In a disclosed embodiment, the physical sensor uses one or more servo-actuated monofilaments to test for skin sensation loss. A monofilament exam is a test used to identify cases of peripheral neuropathy in diabetic patients. This technique is similar in some respects to the Semmes-Weinstein monofilament exam used by physicians, although the administration of the test, features of the testing device, and collection and analysis of the data are different than traditional tests, as described in detail below.

In a disclosed embodiment, the device attaches a series of monofilament fibers with a standard gauge (e.g., a 5.07 gauge fiber that produces 10 g of pressure) to micro-servo actuators placed in locations distributed around the device in order to contact test sites of the body part to be measured. On a foot, illustrative test site locations include the heel, foot arch, ball of the foot, behind the toes, and the big toe. The test may be administered with an interactive user interface, such as an interactive voice system. (As an alternative or in addition to the interactive voice system, the user interface may be implemented as a graphical user interface (e.g., with a touch screen) or in some other way.) The user interface may, for example, provide instructions to the patient on how to start the test or prompt the patient (e.g., using a recorded or synthesized voice output) to say or otherwise indicate (e.g., with a button press, a gesture or other user input) when they feel a sensation from the monofilament. Responses from the patient can then be processed, recorded, and acted upon by the system as described herein.

Other physical sensing or testing mechanisms may be used in combination with or in place of monofilament tests. For example, the system may include circuitry embedded in the foot platform to test the user's ability to feel heat or pain by means of integrated heating strips or low-current electrical discharges. In such embodiments, a heat-testing device may use an optically transparent but electrically conductive material such as indium tin oxide to conduct current to the test site where it is run through a higher-resistance portion of the coating in order to generate resistive heating, similar to the way aircraft window heaters work. As in other embodiments described herein, the user may then be prompted (e.g., using a recorded or synthesized voice output) to say or otherwise indicate (e.g., with a button press, a gesture or other user input) when they feel a sensation from the heating element. The heat sensitivity testing method may include several different levels of heating to test for sensation to obtain a more accurate assessment of the level of neuropathy present. An electrical discharge device may use transparent conductive material to route a circuit to several test sites located around the foot (or other body part being tested). A small gap is left for the user's body to complete the circuit and introduce electrical stimulation. This may be done with high-voltage, low-current electricity as is commonly used in other medical diagnostic equipment to test for pain responses. Again, the user is prompted to indicate when they feel the stimulus. The intensity of the discharge can be varied to obtain a more accurate assessment of the level of neuropathy present.

In a disclosed embodiment, the sensors and related structures and control circuitry are combined and integrated into a standing scale form factor. A standing scale (e.g., a bathroom scale) provides a surface on which a person may stand, which provides a suitable platform for foot-based data collection. This disclosed embodiment also has the benefit of collecting the user's weight, which is also an important metric for diabetic patients, since weight management is often an important part of a diabetes management regimen.

Figure 1:
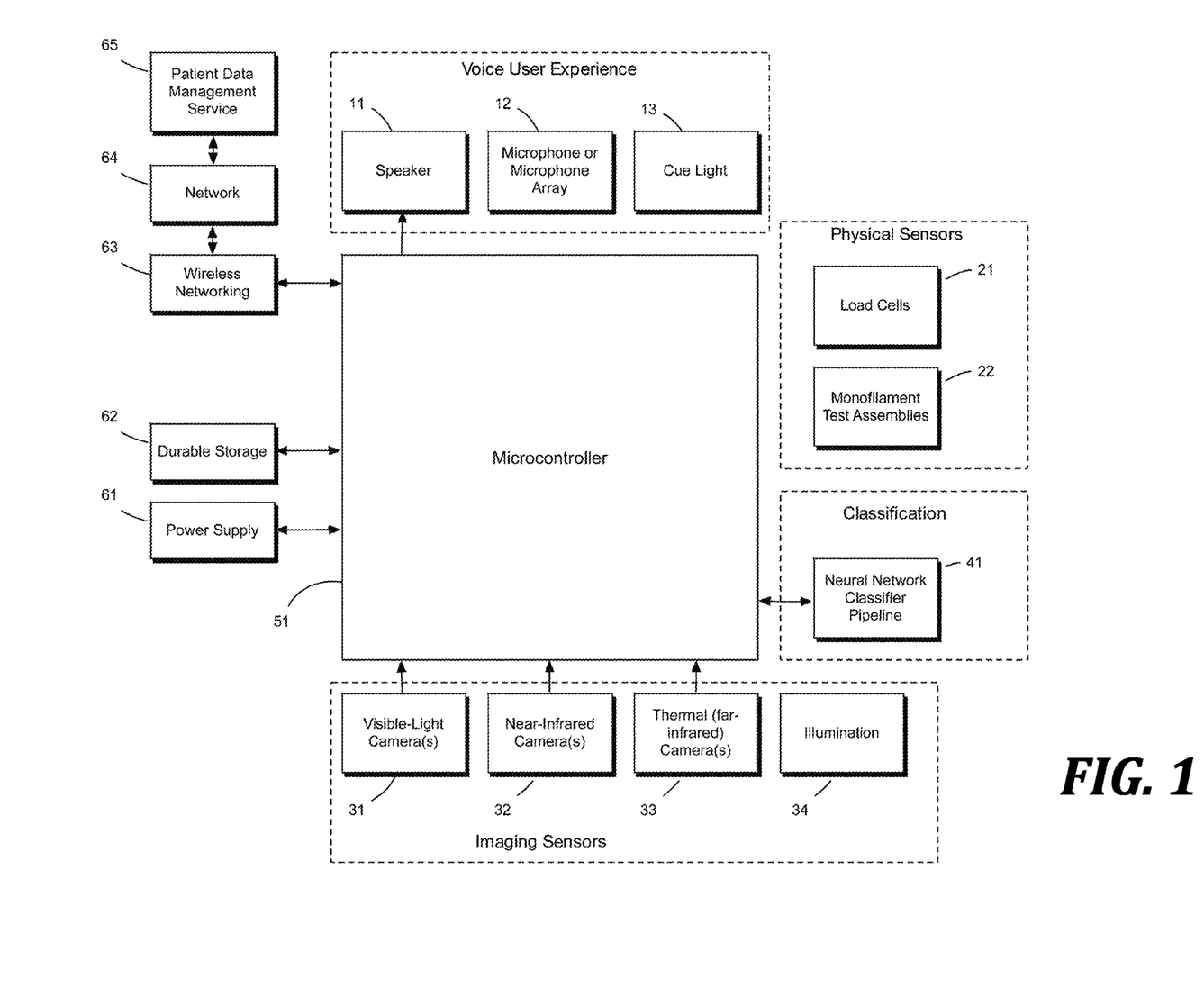
FIG. 1 is a block diagram that depicts electronic systems that may be used in disclosed embodiments.

FIG. 1 is a block diagram that depicts electronic systems that may be used in disclosed embodiments. In the example shown in FIG. 1, microcontroller 51 controls program execution and sensor integration, and is powered by a low voltage power supply 61, and uses a durable storage device 62, such as a magnetic hard drive or static flash drive, for program and data storage. Alternatively, the device may be controlled by some other controller or computing device.

FIG. 1 also depicts an illustrative user interface in the form of an interactive voice system. The interactive voice system provides a user experience which makes use of a speaker 11 to provide audio output and microphones with related speech recognition software or hardware to listen for user commands and responses to questions. The interactive voice system may use a single microphone or an array of microphones 12, which may be organized for beamforming for better background noise rejection. The illustrative user interface also uses a visual indicator, such as a multi-color cue light 13, to indicate various interface states. In this example, the cue light 13 may be used to indicate states such as microphone active, microphone muted, system busy (e.g., when capturing an image or processing a captured image), and when the system is speaking or providing other output.

During operation, the system may obtain data from one or more sensors, which may be physical or optical. In the example shown in FIG. 1, a collection of load cells 21, which may be arranged in groups of four, are used to measure the user's weight. The system may self-tare to subtract the weight of other device equipment such as the footbed, electronics, and cameras. For example, the system may perform self-taring during device initialization, before the first user weigh-in. Load cells may be connected to the microcontroller by way of an analog-to-digital amplifier/converter such as the AVIA Semiconductor HX711.

In some embodiments, the device also includes an array of monofilament probe assemblies 22 that are used to test the user's foot for peripheral neuropathy. These are described in more detail in FIG. 3.

The device uses optical image sensors (e.g., in the form of cameras) to create images of the user's feet (or other body areas in some embodiments). In the example shown in FIG. 1, visible-light cameras 31 are used, along with other cameras that capture images at other wavelengths. In some embodiments, to reduce cost and complexity visible light cameras 31 may be commercially available cameras with visible-light image sensors such as those found in cellular phones. Other cameras may use image sensors calibrated to capture visible light, near-infrared light, infrared light, or some combination thereof. In some embodiments, wide-angle lenses may be used in conjunction with image sensors to enable more compact chassis design, such as for cameras mounted below a foot platform. Near-infrared cameras 32 may be used to capture extended spectrum information. Described embodiments may include one or more illumination sources 34 (e.g., LED lights) that provide more consistent image lighting for visible-light and/or near-infrared image sensors. Consistent image lighting can improve image classifier accuracy.

Some embodiments use thermal image sensors to capture heat data about the user's body. In the example shown in FIG. 1, thermal image sensors are included in thermal (far-infrared) cameras 33. Thermal imaging applied to skin provides the ability to indicate areas of concern, such as skin regions where the skin is cooler than surrounding skin, possibly indicating lower-than-normal blood supply, which could indicate a likely area for the development of peripheral neuropathy. Alternately, a skin region that is higher temperature than the surrounding skin may indicate the development of an infection such as a diabetic foot ulcer.

In some embodiments, subsequent to collection of optical imaging data, the images are provided as input to image processing software, such as a neural network classifier pipeline 41, which then performs a series of classification steps related to diagnosis or treatment. Some exemplary classification steps include, for example, detecting the presence, position and orientation of feet (or other body parts); detecting the presence and location of skin abnormalities (e.g., ulcers, foreign objects, or abnormal temperatures); and classifying these abnormalities (e.g., as possible areas of peripheral neuropathy or infection). In each of these steps, good results can be obtained by using a deep convolutional neural network. Many existing commercial and open-source frameworks can be used for this task. Basic principles of training classifiers are well known to those skilled in the art of machine learning, and these basic principles need not be described here.

In described embodiments, training classifiers involves collecting extensive datasets of feet (or other body parts), both with and without skin abnormalities being searched for, manually labeling this data with the correct classification labels for each step in the classification pipeline (e.g., presence, position, orientation of feet, or presence and location of skin abnormalities, types of abnormalities). This data is then used to train the machine-learned classifiers and iteratively improve the classifier accuracy by obtaining new data, adjusting the steps in the classification pipeline, extracting new features to assist in classification, etc. The overall classifier pipeline prediction can be measured with the precision of the predictions (e.g., the percentage of predictions that correctly find positive results) and the recall of the predictions (e.g., percentage of truly positive results that result in positive predictions). These metrics can be balanced in order to obtain an acceptable tradeoff between the two.

The classification pipeline output may be multi-class; for example, it may identify diabetic foot ulcers as well as other foot conditions such as cuts, bruises, corns, warts, etc. The classification pipeline output may alternately output a binary classification indicating whether a given skin issue requires further medical follow-up. The binary classification approach may be useful in situations where an abnormality is detected to be present but, due to factors such as poor image quality or missing images, the abnormality cannot be accurately classified.

Some embodiments send data (e.g., patient weight data, raw image data, image classification data) to other devices for storage or further processing. For example, data may be transmitted through a wireless networking adapter 63 and then through a network 64 to arrive at a remote computer system, such as a patient data management service 65. This service may store weight data, raw images, classifier output, or other data and perform further image processing, test the data against predefined rules such as having positive classifier predictions or weight gains above some threshold, and communications such as patient follow up messages. For example, in some embodiments a positive classification reading for foot ulcers may trigger a computer system (e.g., the patient data management service 65) to send an alert to the patient or the patient's care team for follow-up, and send a report (e.g., including images) directly into the patient's electronic medical records.

Figure 4:
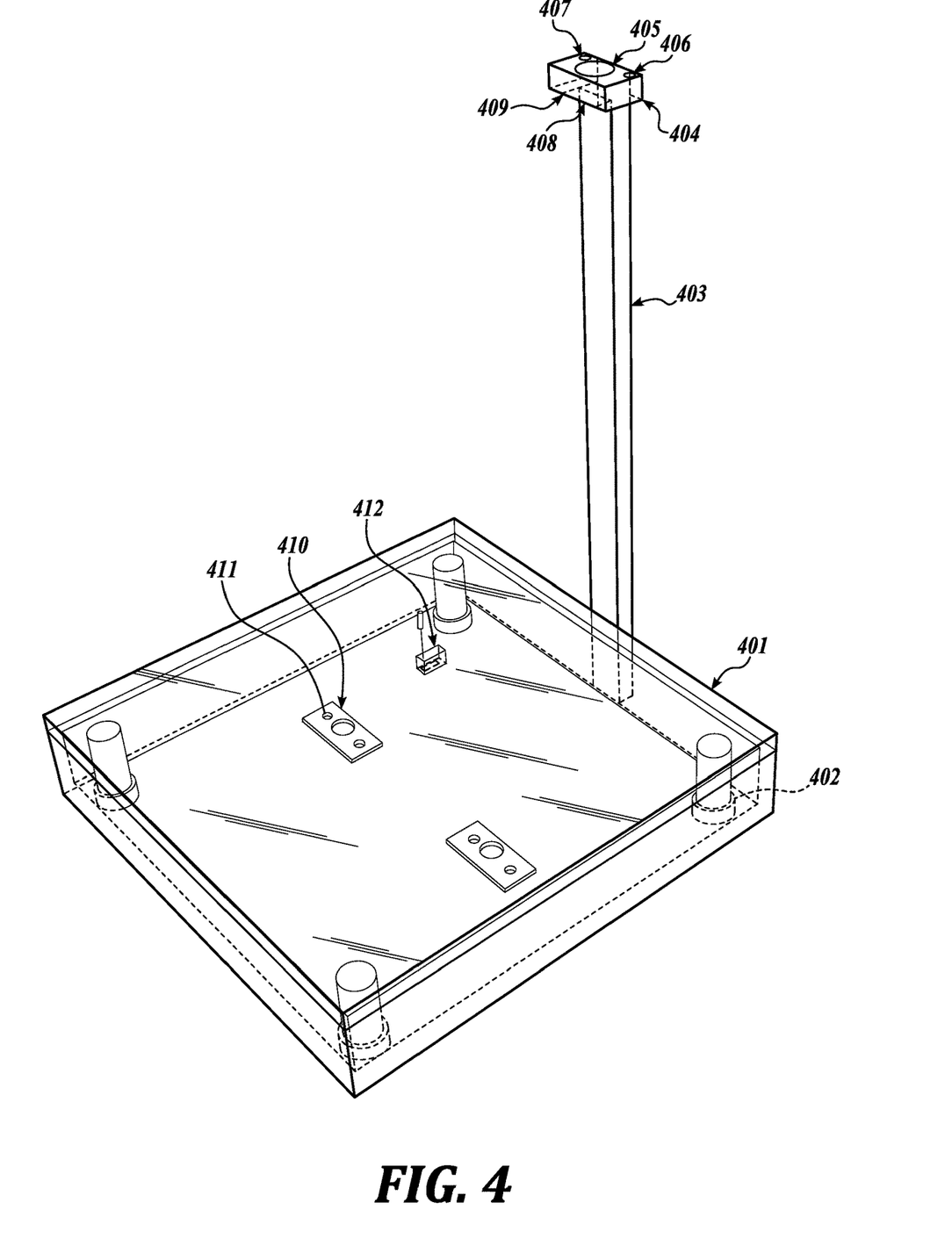
FIG. 4 is a perspective view of a disclosed embodiment integrated in a standing scale.

FIG. 4 is a perspective view of a disclosed embodiment integrated in a standing scale. In the example shown in FIG. 4, the device includes a suitably sized foot platform 401 for the user to stand on during use. (Although embodiments described herein refer to users standing on the platform, it should be readily understood that in other embodiments the device can be modified, such as with a bench or chair, such that the user is not required to stand.) The platform 401 may be constructed of a strong transparent material such as polycarbonate or tempered glass in order to provide the ability for upward-facing cameras 410 to image the bottoms of the user's feet. The transparent material may be selected based on the imaging to be performed. For example, to allow thermographic cameras to capture images through the foot platform, a suitable material that is transparent to longinfrared wavelengths may be used. Built-in illumination 411, such as LED lights, may be used to provide consistent and sufficient lighting for the images. To capture images of the user's feet at close range, the cameras 410 may include wide angle lenses, and may be arranged in an array. This design allows the platform 401 to be constructed with a low profile, which reduces the likelihood of injury due to tripping or falling when using the device. In one embodiment, the footbed measures 12 inches×12 inches, and uses a pair cameras with 150° field of view to obtain full coverage of the footbed at a range of approximately 3.2 inches. In this example, the optical distortion of these cameras is minimal enough to not require any special processing, and give clear corner-to-corner resolution.

The platform 401 is supported by four load cells, which are in turn supported by support legs 402. The load cells are used to measure the weight of the user. For mechanical simplicity and to prevent binding or friction, which may produce inaccurate weight measurements, other components on the device may be attached to the foot platform 401. The weight of the foot platform and other components attached to it may be tared by the device during an automatic taring process, which may be performed during device power-up, device restart, or at some other time.

In some situations, imaging of the tops of the user's feet may be desirable. For this type of imaging, image sensors may be included in an upper head assembly 404 attached to a support arm 403. The upper head assembly also may include elements of a user interface, which may be beneficial for locating the user interface closer to the user's head to allow the user to more easily interact with the user interface (e.g., to more easily detect the user's voice in a user interface with voice control functionality). In the example shown in FIG. 4, the upper head assembly 404 includes a speaker 405 and a microphone 406 to support voice interactions with the user, as well as a visual indicator such as a multi-color cue light 407 to indicate interface states such as microphone active, microphone muted, system busy, system speaking (e.g., providing synthesized or recorded voice output), or error conditions. Image sensors in the upper head assembly 404 may include cameras 408 such as visible-light, near-infrared, and thermographic cameras, along with built-in illumination 409 in order to provide sufficient and consistent lighting for the images.

As mentioned above, some embodiments are equipped with one or more monofilament assemblies 412 to perform monofilament exams. Although only one monofilament assembly is shown in FIG. 4 for ease of illustration, the device may include several assemblies placed at various locations around the device in order to test different sites on the user's feet. A foot outline (not shown) or other visual or tactile guide may be provided on the foot platform 401 to assist users in positioning their feet correctly for imaging or monofilament testing.

Figure 5:
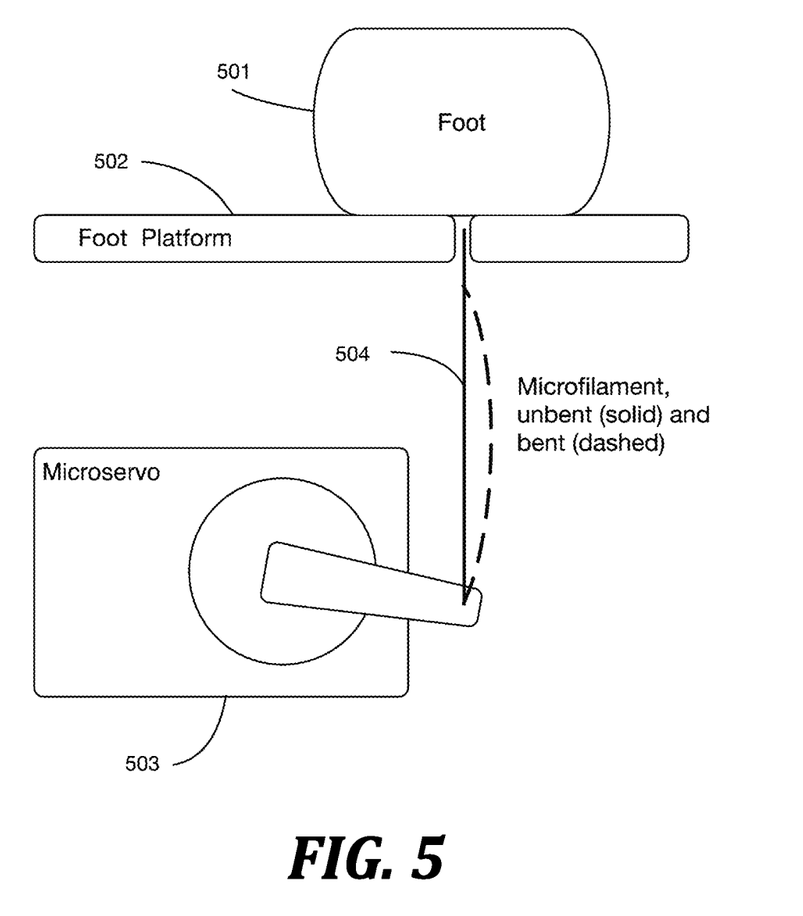
FIG. 5 is a schematic diagram of a monofilament assembly that may be used in described embodiments for peripheral neuropathy testing.

FIG. 5 is a schematic diagram of a monofilament assembly that may be used in described embodiments for peripheral neuropathy testing. In described embodiments, the test is derived from the Semmes-Weinstein monofilament exam used by physicians. During operation, an actuator (e.g., micro servo actuator 503) is activated to move the monofilament 504 through an opening in the foot platform 502 so that the monofilament 504 is in contact with the user's foot 501. Various forms of actuation are contemplated, including a rotary servo with an arm that is connected to the monofilament, or a linear actuator. As shown in FIG. 5, the actuation occurs with sufficient force to cause the monofilament to bend or buckle below the foot platform 501. The device can be designed to ensure that a consistent amount of pressure is applied during testing. In at least one embodiment, the monofilament is pre-calibrated to a standard amount of buckling force, e.g., 10 grams.

Figure 2:
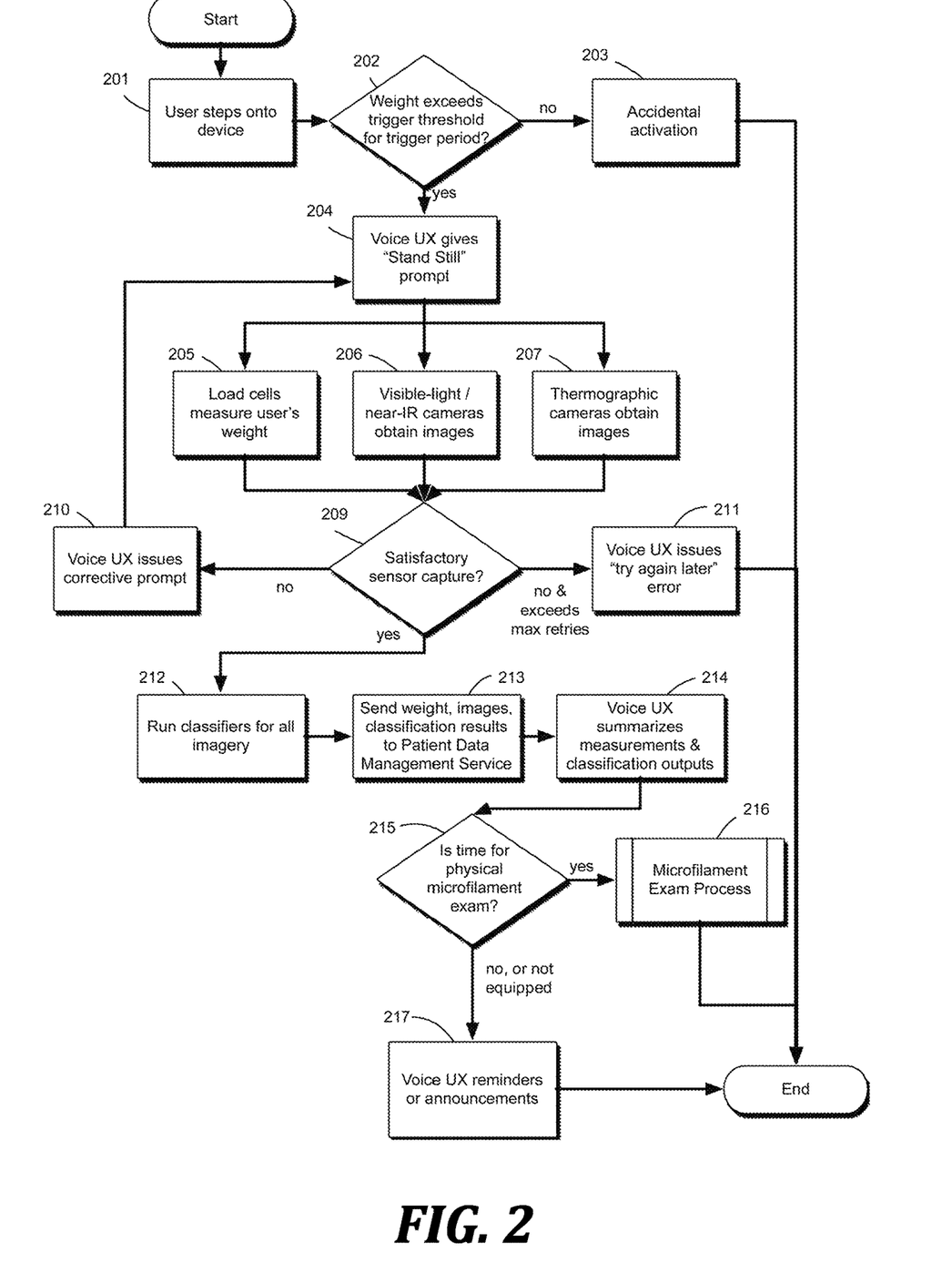
FIG. 2 is a flow chart that describes an illustrative weight-activated data collection and analysis workflow that may be used in disclosure embodiments.

FIG. 2 is a flow chart that describes an illustrative weight-activated data collection and analysis workflow in a disclosed embodiment. In the example shown in FIG. 2, when a user steps onto the foot platform at step 201, the device is activated. The device collects the weight over the course of a trigger period (e.g., a few seconds) and compares this to its trigger threshold weight (e.g., 10 pounds) and trigger period (e.g., one second) at step 202. If the measured weight is below the threshold weight, or the weight is present for less than the trigger period, the activation is assumed to be accidental at step 203, and the workflow ends. Other embodiments may use different thresholds for weight and trigger periods, or such thresholds may be omitted if not deemed necessary for a particular application.

In the example shown in FIG. 2, if the threshold weight is measured for the trigger period, the user will be prompted (e.g., with synthesized or recorded voice output from the speaker 11) to stand still at step 204, since imaging can take a few seconds and remaining motionless during the image capture process may help the system to obtain higher quality images. The device can then, concurrently or in series, use load cells at step 205 to measure the user's weight, use visual light and/or near-infrared image sensors to capture images of the user's feet at step 206, and use infrared imaging sensors to obtain thermographic images of the user's feet at step 207. Data obtained in steps 205, 206, and 207 can then be tested in step 209 using a classifier or other image analysis or pattern recognition techniques.

With regard to images, the system can use techniques such as edge detection to ensure that quality, lighting, and body positioning are satisfactory for input into the image classification pipeline. For example, if image analysis indicates blurry edges in locations where clear edges are expected, or if one foot is detected when two feet are expected, the system may infer that the user was not standing still or not positioned correctly during the image capture. The determination as to whether the input data are satisfactory may vary depending on implementation. If the inputs are found to be deficient, the user interface may prompt the user to take corrective action at step 210. For example, if one of the user's feet was not positioned for a clear view from the camera, the user interface may prompt the user to move that foot back onto the foot platform. After suggesting corrective action, the device then attempts to obtain new sensor inputs and returns to step 204. If satisfactory sensor data cannot be obtained (e.g., after a threshold number of collection attempts), the user interface may prompt the user to try again later at step 211 and end the workflow.

Once satisfactory sensor inputs are obtained, the inputs are processed further. For example, images may be passed to a neural network classifier pipeline that classifies the images at step 212. After classification—which may indicate the presence or absence of conditions like diabetic foot ulcers—the system may upload data such as classification results, raw images, and the user's weight to a patient data management service at step 213. While some embodiments may upload data, such as the sensor and classification data, to other computing devices, this is not required. For example, standalone devices that do not use a network connection or a patient data management service are contemplated. In other scenarios, such as cloud computing arrangements, the system may omit local classification or image analysis and transmit only raw images, or images and weight data, to an external system or server that performs more intensive processing, such as image analysis and classification.

Referring again to the example shown in FIG. 2, after classification has occurred, the user interface provides the user with a summary of the process so far at step 214, which may include measurements and classification outputs. The system may provide, for example, the user's weight, how measurements such as weight may be trending compared with previous measurements, and an assessment of whether any problematic issues were detected.

In some embodiments or usage scenarios, the summary provided to the user at step 214 will mark the end of the workflow. In other embodiments or scenarios, the workflow may proceed with further examination of the user. In the example shown in FIG. 2, in embodiments equipped with monofilament probes, the system will check if it is time to perform a monofilament examination at step 215. This check could be based on a scheduled examination period, or it could be a rule-based action based on results observed from the previous steps in the exam. For example, if a thermographic camera detects hot or cold spots (skin regions that are cooler or warmer than surrounding regions), these conditions could be cross-verified with a physical monofilament exam. If the monofilament examination is to be performed, the system initiates the monofilament exam process at step 216. If the device is not equipped with a monofilament examination device, or if it is not time for a monofilament exam, the user interface concludes the measurement session by reminding the user of any important information that may be pertinent at step 217. For example, this might include the date of their next monofilament exam, or if the user is following a larger care plan, it may include other aspects of disease management like tips for healthy eating, reminders to exercise, and so on. The workflow then ends.

Many alternatives to the workflow of FIG. 2 are possible. For example, the system may omit providing a summary of the procedure, or the system may provide the summary at some other time or in some other way. For example, if the device is located in a public area such as a pharmacy, the device may provider the user with the option to receive an email or other communication indicating results of the test for privacy reasons, rather than providing them as audible voice output to the user.

Figure 3:
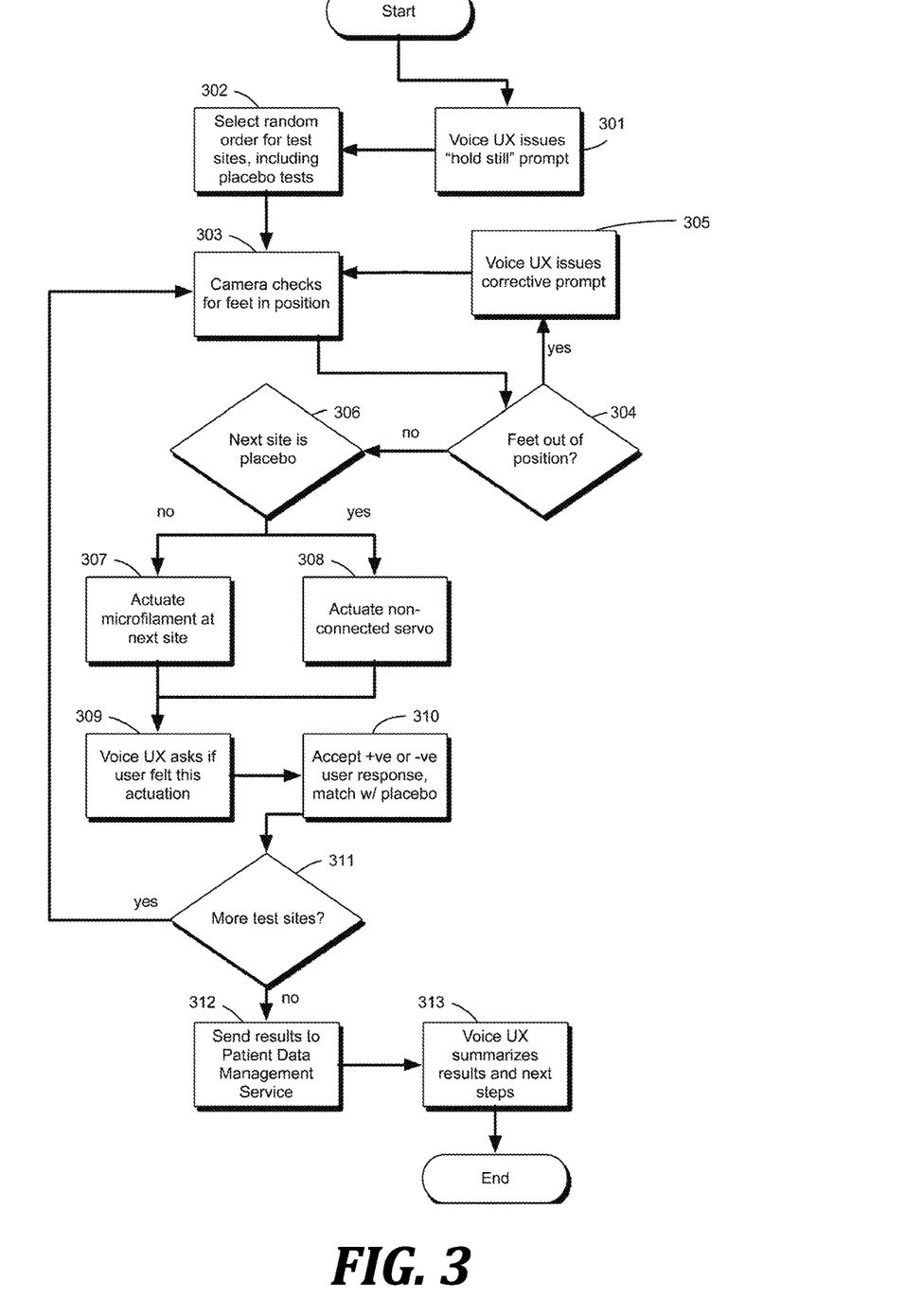
FIG. 3 is a flowchart of an illustrative monofilament exam workflow that may be used in disclosure embodiments.

FIG. 3 is a flowchart of an illustrative monofilament exam workflow. In some embodiments, the monofilament exam is initiated while a user is standing on the device, as part of a weight-activated workflow, such as the workflow illustrated in FIG. 2. The user interface prompts the user to stand still at step 301, since the monofilament exam may take a couple of minutes or more to complete. The user interface may provide an indicator, such as a visual countdown timer or feedback from the cue light, to indicate that the exam is in progress or estimated time remaining. The device selects test sites for monofilament tests at step 302. In this example, the device selects a random order for the test sites where monofilament tests will be actuated, and may also include one or more placebo measurements. Alternatively, the device may perform the exam according to a predetermined order of test sites or placebo measurements, or select from among a set of possible orders of test sites or placebo measurements.

The device then uses the imaging system in combination with further processing (e.g., a classifier or other image analysis algorithm such as edge detection) to check if the user's feet are in a proper position at step 303. If the feet are out of position at step 304, the user interface prompts the user to take corrective action at step 305. Once the user's feet are properly positioned, the system determines whether the first test site is a placebo measurement at step 306. If the action performed at the site is a non-placebo measurement, the relevant monofilament test assembly for that test site is actuated at step 307. If the action performed at the test site is a placebo measurement, a monofilament probe assembly that does not contact the user's foot will be actuated at step 308. Placebo tests may be used to test for false-positive responses by the user. Since the monofilament exam actuators may generate a certain amount of noise and vibration during an actual exam, in a placebo test it may be important to actually perform a physical actuation to simulate the noise and vibration of a real exam and accurately test for false-positive response.

Following either the placebo measurement or the actual exam at the test site, the user interface prompts the user to indicate if they felt the last touch at step 309. The user can then respond with an affirmative or negative response at step 310, which the system will match against the test that was actually performed. At step 311, the system determines whether there are more sites to be tested or placebo measurements to be performed. If so, steps 303-310 may be repeated for subsequent test sites or placebo measurements in the set selected at step 302. Once all sites have been tested and any placebo measurements have been performed, the results, including which test sites were actuated and how the user responded, may be uploaded to a patient data management service at step 312. Some embodiments may use the device as a standalone device without the use of a patient data management service, in which case this step may be skipped. The user interface summarizes the results for the user at step 313. This summary may include listing how many sites were tested, how many the user was able to correctly identify, and a list of any test sites where the user did not feel a real actuation.

Many alternatives to the workflow of FIG. 3 are possible. For example, the system may omit providing a summary of the procedure, or the system may provide the summary at some other time or in some other way. For example, if the device is located in a public area such as a pharmacy, the device may provider the user with the option to receive an email or other communication indicating results of the test for privacy reasons, rather than providing them as audible voice output to the user.

Illustrative Computing Devices and Operating Environments

Unless otherwise specified in the context of specific examples, computing techniques and related tools described herein may be implemented by any suitable computing device or set of devices.

In any of the described examples, an engine may be used to perform actions. An engine includes logic (e.g., in the form of computer program code) configured to cause one or more computing devices to perform actions described herein as being associated with the engine. For example, a computing device can be specifically programmed to perform the actions by having installed therein a tangible computer-readable medium having computer-executable instructions stored thereon that, when executed by one or more processors of the computing device, cause the computing device to perform the actions. The particular engines described herein are included for ease of discussion, but many alternatives are possible. For example, actions described herein as associated with two or more engines on multiple devices may be performed by a single engine. As another example, actions described herein as associated with a single engine may be performed by two or more engines on the same device or on multiple devices.

Some of the functionality described herein may be implemented in the context of a client-server relationship. In this context, server devices may include suitable computing devices configured to provide information and/or services described herein. Server devices may include any suitable computing devices, such as dedicated server devices. Server functionality provided by server devices may, in some cases, be provided by software (e.g., virtualized computing instances or application objects) executing on a computing device that is not a dedicated server device. The term "client" can be used to refer to a computing device that obtains information and/or accesses services provided by a server over a communication link. However, the designation of a particular device as a client device does not necessarily require the presence of a server. At various times, a single device may act as a server, a client, or both a server and a client, depending on context and configuration. Actual physical locations of clients and servers are not necessarily important, but the locations can be described as "local" for a client and "remote" for a server to illustrate a common usage scenario in which a client is receiving information provided by a server at a remote location. Alternatively, a peer-to-peer arrangement, or other models, can be used.

Figure 6:
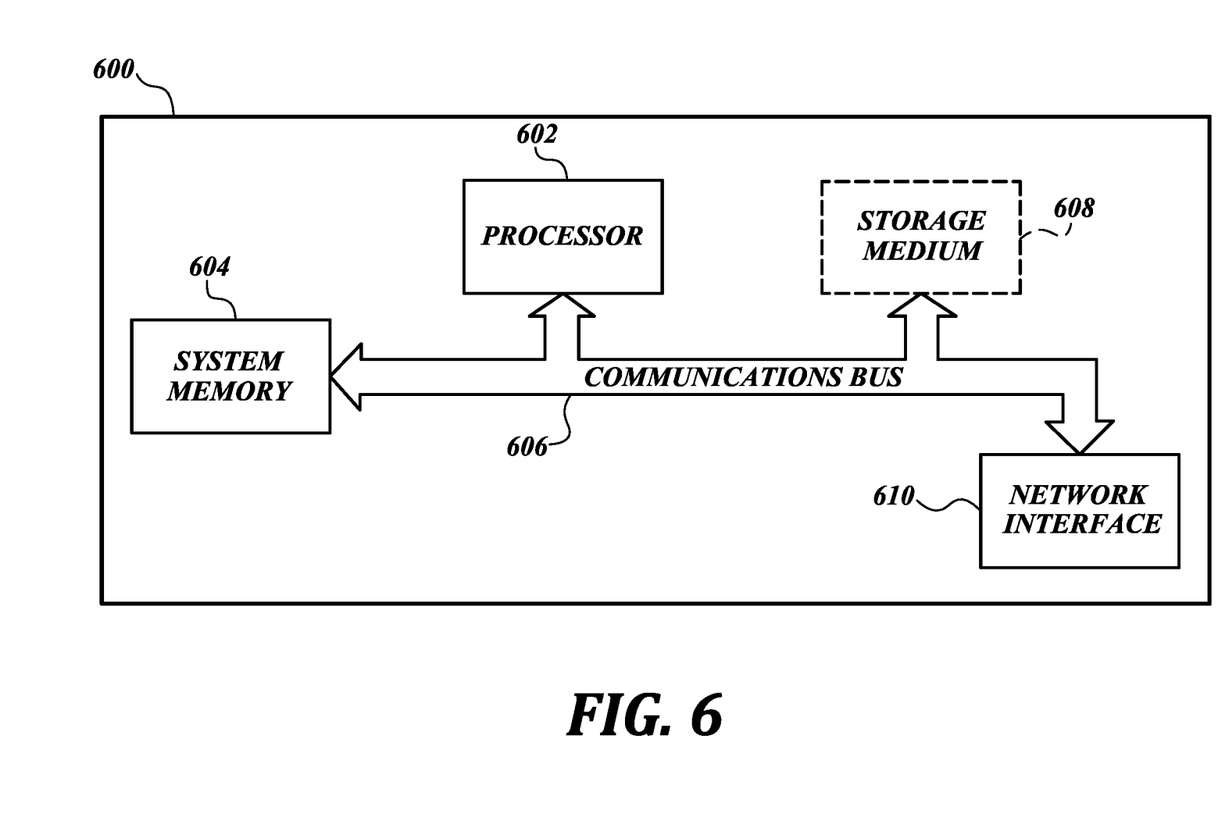
FIG. 6 is a block diagram that illustrates aspects of an illustrative computing device appropriate for use in accordance with embodiments of the present disclosure.

FIG. 6 is a block diagram that illustrates aspects of an illustrative computing device 600 appropriate for use in accordance with embodiments of the present disclosure. The description below is applicable to servers, personal computers, mobile phones, smart phones, tablet computers, embedded computing devices, and other currently available or yet-to-be-developed devices that may be used in accordance with embodiments of the present disclosure.

In its most basic configuration, the computing device 600 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or other memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as WiFi, 2G, 3G, 4G, LTE, WiMAX, Bluetooth, and/or the like.

In FIG. 6, the computing device 600 also includes a storage medium 608. However, services may be accessed using a computing device that does not include means for persisting data to a local storage medium. Therefore, the storage medium 608 depicted in FIG. 6 is optional. In any event, the storage medium 608 may be volatile or nonvolatile, removable or nonremovable, implemented using any technology capable of storing information such as, but not limited to, a hard drive, solid state drive, CD-ROM, DVD, or other disk storage, magnetic tape, magnetic disk storage, and/or the like.

As used herein, the term "computer-readable medium" includes volatile and nonvolatile and removable and nonremovable media implemented in any method or technology capable of storing information, such as computer-readable instructions, data structures, program modules, or other data. In this regard, the system memory 604 and storage medium 608 depicted in FIG. 6 are examples of computer-readable media.

For ease of illustration and because it is not important for an understanding of the claimed subject matter, FIG. 6 does not show some of the typical components of many computing devices. In this regard, the computing device 600 may include input devices, such as a keyboard, keypad, mouse, trackball, microphone, video camera, touchpad, touchscreen, electronic pen, stylus, and/or the like. Such input devices may be coupled to the computing device 600 by wired or wireless connections including RF, infrared, serial, parallel, Bluetooth, USB, or other suitable connection protocols using wireless or physical connections.

In any of the described examples, input data can be captured by input devices and processed, transmitted, or stored (e.g., for future processing). The processing may include encoding data streams, which can be subsequently decoded for presentation by output devices. Media data can be captured by multimedia input devices and stored by saving media data streams as files on a computer-readable storage medium (e.g., in memory or persistent storage on a client device, server, administrator device, or some other device). Input devices can be separate from and communicatively coupled to computing device 600 (e.g., a client device), or can be integral components of the computing device 600. In some embodiments, multiple input devices may be combined into a single, multifunction input device (e.g., a video camera with an integrated microphone). The computing device 600 may also include output devices such as a display, speakers, printer, etc. The output devices may include video output devices such as a display or touchscreen. The output devices also may include audio output devices such as external speakers or earphones. The output devices can be separate from and communicatively coupled to the computing device 600, or can be integral components of the computing device 600. Input functionality and output functionality may be integrated into the same input/output device (e.g., a touchscreen). Any suitable input device, output device, or combined input/output device either currently known or developed in the future may be used with described systems.

In general, functionality of computing devices described herein may be implemented in computing logic embodied in hardware or software instructions, which can be written in a programming language, such as C, C++, COBOL, JAVA™, PHP, Perl, Python, Ruby, HTML, CSS, JavaScript, VBScript, ASPX, Microsoft .NET™ languages such as C#, and/or the like. Computing logic may be compiled into executable programs or written in interpreted programming languages. Generally, functionality described herein can be implemented as logic modules that can be duplicated to provide greater processing capability, merged with other modules, or divided into sub-modules. The computing logic can be stored in any type of computer-readable medium (e.g., a non-transitory medium such as a memory or storage medium) or computer storage device and be stored on and executed by one or more general-purpose or special-purpose processors, thus creating a special-purpose computing device configured to provide functionality described herein.

Extensions and Alternatives

Many alternatives to the systems and devices described herein are possible. For example, individual modules or subsystems can be separated into additional modules or subsystems or combined into fewer modules or subsystems. As another example, modules or subsystems can be omitted or supplemented with other modules or subsystems. As another example, functions that are indicated as being performed by a particular device, module, or subsystem may instead be performed by one or more other devices, modules, or subsystems. Although some examples in the present disclosure include descriptions of devices comprising specific hardware components in specific arrangements, techniques and tools described herein can be modified to accommodate different hardware components, combinations, or arrangements. Further, although some examples in the present disclosure include descriptions of specific usage scenarios, techniques and tools described herein can be modified to accommodate different usage scenarios. Functionality that is described as being implemented in software can instead be implemented in hardware, or vice versa.

Many alternatives to the techniques described herein are possible. For example, processing stages in the various techniques can be separated into additional stages or combined into fewer stages. As another example, processing stages in the various techniques can be omitted or supplemented with other techniques or processing stages. As another example, processing stages that are described as occurring in a particular order can instead occur in a different order. As another example, processing stages that are described as being performed in a series of steps may instead be handled in a parallel fashion, with multiple modules or software processes concurrently handling one or more of the illustrated processing stages. As another example, processing stages that are indicated as being performed by a particular device or module may instead be performed by one or more other devices or modules.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for automated diagnosis of a diabetic foot condition, the method comprising:
   capturing, by one or more image capture devices of a medical diagnostic apparatus, optical image data of a target area of a foot;
   collecting, by a touch sensitivity testing device of the medical diagnostic apparatus, physical touch sensitivity data for the target area of the foot;
   transmitting, by the medical diagnostic apparatus, the optical image data and the physical touch sensitivity data to an analysis engine, wherein the analysis engine comprises a neural network classifier pipeline; and
   outputting, by the analysis engine, one or more indications of a diabetic foot condition,
   wherein the neural network classifier pipeline of the analysis engine automatically performs classification steps on the optical image data to generate the one or more indications of a diabetic foot condition, and wherein the classification steps performed by the neural network classifier pipeline include:
   detecting presence, position, and orientation of the foot;
   detecting presence and location of a skin abnormality on the foot; and
   classifying the detected skin abnormality as a diabetic foot ulcer.

2. The method of claim 1 further comprising checking the optical image data for one or more of image quality, lighting conditions, or body positioning.

3. The method of claim 1 further comprising, prior to collecting the physical touch sensitivity data, confirming the position of the foot based at least in part on the optical image data.

4. The method of claim 1, wherein the touch sensitivity testing device comprises a servo-actuated monofilament probe.

5. The method of claim 1, wherein the neural network classifier pipeline of the analysis engine comprises a deep convolutional neural network.

6. The method of claim 1 further comprising outputting, by the analysis engine, a binary classification for medical follow-up in a case where the analysis engine determines that the neural network classifier pipeline cannot accurately classify the detected skin abnormality based on the optical image data.

7. A non-transitory computer-readable medium having stored therein instructions configured to cause one or more computing devices to cause steps to be performed for automated diagnosis of a diabetic foot condition, the steps comprising:
   capturing, by one or more image capture devices of a medical diagnostic apparatus, optical image data of a target area of a foot;
   collecting, by a touch sensitivity testing device of the medical diagnostic apparatus, physical touch sensitivity data for the target area of the foot;
   transmitting, by the medical diagnostic apparatus, the optical image data and the physical touch sensitivity data to an analysis engine, wherein the analysis engine comprises a neural network classifier pipeline; and
   outputting, by the analysis engine, one or more indications of a diabetic foot condition,
   wherein the neural network classifier pipeline of the analysis engine automatically performs classification steps on the optical image data to generate the one or more indications of a diabetic foot condition, and wherein the classification steps performed by the neural network classifier pipeline include:
   detecting presence, position, and orientation of the foot;
   detecting presence and location of a skin abnormality on the foot; and
   classifying the detected skin abnormality as a diabetic foot ulcer.

8. The non-transitory computer-readable medium of claim 7, the steps further comprising checking the optical image data for one or more of image quality, lighting conditions, or body positioning.

9. The non-transitory computer-readable medium of claim 7, the steps further comprising, prior to collecting the physical touch sensitivity data, confirming the position of the foot based at least in part on the optical image data.

10. The non-transitory computer-readable medium of claim 7, wherein the touch sensitivity testing device comprises a servo-actuated monofilament probe.

11. The non-transitory computer-readable medium of claim 7, wherein the neural network classifier pipeline of the analysis engine comprises a deep convolutional neural network.

12. The non-transitory computer-readable medium of claim 7, the steps further comprising causing the analysis engine to output a binary classification for medical follow-up in a case where the analysis engine determines that the neural network classifier pipeline cannot accurately classify the detected skin abnormality based on the optical image data.

13. A computer system comprising one or more computing devices programmed to perform steps for automated diagnosis of a diabetic foot condition, the steps comprising:
 causing one or more image capture devices of a medical diagnostic apparatus to capture optical image data of a target area of a foot;
 causing a touch sensitivity testing device of the medical diagnostic apparatus to collect physical touch sensitivity data for the target area of the foot;
 causing the medical diagnostic apparatus to transmit the optical image data and the physical touch sensitivity data to an analysis engine, wherein the analysis engine comprises a neural network classifier pipeline; and
 obtaining one or more indications of a diabetic foot condition from the analysis engine,
 wherein the neural network classifier pipeline of the analysis engine automatically performs classification steps on the optical image data to generate the one or more indications of a diabetic foot condition, and wherein the classification steps performed by the neural network classifier pipeline include:
  detecting presence, position, and orientation of the foot;
  detecting presence and location of a skin abnormality on the foot; and
  classifying the detected skin abnormality as a diabetic foot ulcer.

14. The computer system of claim 13, the steps further comprising checking the optical image data for one or more of image quality, lighting conditions, or body positioning.

15. The computer system of claim 13, the steps further comprising, prior to collecting the physical touch sensitivity data, confirming the position of the foot based at least in part on the optical image data.

16. The computer system of claim 13, wherein the touch sensitivity testing device comprises a servo-actuated monofilament probe.

17. The computer system of claim 13, wherein the neural network classifier pipeline of the analysis engine comprises a deep convolutional neural network.

18. The computer system of claim 13, wherein the one or more computing devices are further programmed to cause the analysis engine to output a binary classification for medical follow-up in a case where the analysis engine determines that the neural network classifier pipeline cannot accurately classify the detected skin abnormality based on the optical image data.

* * * * *